US00PP08552P

United States Patent [19]

Trees

[11] Patent Number: Plant 8,552

[45] Date of Patent: Jan. 18, 1994

[54] GERANIUM PLANT 'DESIGNER LIGHT PINK'

[75] Inventor: Scott C. Trees, Nipomo, Calif.

[73] Assignee: Ball Floraplant, a division of Geo. J. Ball, Inc., West Chicago, Ill.

[21] Appl. No.: 996,116

[22] Filed: Dec. 23, 1992

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Arnold, White & Durkee

[57] ABSTRACT

Geranium Designer Series TM Light Pink (BFP-174) is a new and distinct cultivar of Geranium, botanically known as Pelargonium×hortorum Bailey, and hereinafter referred to by the cultivar name Designer Light Pink. Designer Light Pink was selected from among the progeny of a cross between female parent Romance and PAS-W. The new cultivar is distinguishable from other geraniums and from both parents in not requiring a growth regulator for self-branching.

1 Drawing Sheet

BACKGROUND OF THE NEW PLANT

Designer Light Pink is a product of a planned breeding program which had the objective of creating new Geranium cultivars with medium green foliage, large round umbels, good weather tolerance, self branching characteristics without use of growth regulators, fast rooting and good shipping qualities.

Designer Light Pink was originated from a hybridization made in a controlled breeding program in West Chicago, Ill. The female parent was Romance, which has a semi-double light pink flower and medium green foliage. Romance is a European variety which has tetraploid ploidy and medium umbel size. The male parent of Designer Light Pink was PAS-W, a semi-double white tetraploid seedling with light green foliage. PAS-W is tetraploid and has large umbel size. Shipping characteristics are poor. PAS-W is a nonprotected plant. By comparison with the parents, Designer Light Pink is tetraploid, has large umbel size, good weather tolerance and stable chlorophyll (advantageous in shipping).

Designer Light Pink was discovered and selected as one flowering plant within the progeny of the stated cross by the inventor in a controlled environment in Santa Maria, Calif.

The first act of asexual reproduction of Designer Light Pink was accomplished when vegetative cuttings were taken from the initial selection in a controlled environment in Santa Maria, Calif. by a technician supervised by the inventor. Horticultural examination of selected units demonstrated that the combination of characteristics as herein disclosed for Designer Light Pink are firmly fixed and are retained through successive generations of asexual reproduction.

Designer Light Pink has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

The following traits have been repeatedly observed and are determined to be basic characteristics of Designer Light Pink which in combination distinguish this geranium as a new and distinct cultivar. No growth regulators are required to obtain self-branching plants.

days to first flower in greenhouse is 47.3 days from unrooted direct stuck cuttings, plant height at first flower in greenhouse is 22.9 cm, and plant width at first flower in greenhouse is 33.0 cm.

Of the many conventional cultivars known to the present inventor, the most similar in comparison to Designer Light Pink is Precious (patent pending). Designer Light Pink and Precious are both generally light lavender color but Designer Light Pink differs in color tone, has non-imbricated petals, is more floriforous and, in contrast to Precious, has non-shattering flowers when grown under field conditions. Designer Light Pink exhibits basal branching without pinching. Precious by comparison has less basal branching characteristics and a more upright, non-mounding habit than Designer Light Pink. The petaloids of Designer Light Pink are larger than those of Precious, some as large as 2.1×1.4 cm. Precious has 7–8 large petals and small petaloids. Designer Light Pink has shatter resistance and is more tolerant to shipping, as indicated by less chlorophyll breakdown than Precious. There are also other differences between the two plants, such as differences in bud shape, average umbel diameter and number of umbels per plant.

DESCRIPTION OF THE PHOTOGRAPH

The accompanying color photographs show a top view of the typical flower and foliage characteristics of Designer Light Pink.

The view taken against a dark background illustrates flower color closest to the color values assigned from The Royal Horticultural Society Color Chart.

The view taken against a light background highlights the leaf characteristics.

DESCRIPTION OF THE PLANT

In the following description, color references are made to The Royal Horticultural Society Color Chart. The color values were determined between 9:00–10:00 a.m. on Nov. 10, 1992 under 550 foot candles at Arroyo Grande, Calif. USA.

Classification:

*Botanical.*—*Pelargonium×hortorum* Bailey.

*Commercial.*—Designer Light Pink, Zonal Geranium.

INFLORESCENCE

Umbel:

*Average diameter.*—9.5–10.0 cm.

*Average depth.*—6.5–7.0 cm.

*Peduncle length.*—20–22 cm.

*Pedicel length.*—3.0–3.3 cm.

*Number umbels/plant.*—18–20 on 18 week old field grown plant.

*Number of flowers/umbel.*—24–26.

Corolla:

*Average diameter.*—4.5–4.7 cm.

*Form.*—Semi-double.

*Number of petaloids.*—0–2.

*Color (general tonality from a distance of three meters).*—Light lavender 65B.

*Description of petal form.*—Non-imbricate.

*Color (abaxial).*—65B at margin; 65D at center.

*Color (adaxial).*—65D.

*Petal size.*—Length: 2.5–2.7 cm. Width: 1.9–2.5 cm.

*Number of petals.*—5 (non-imbricate).

Bud:

*Shape.*—Oval-pointed.

*Color (abaxial).*—65A.

*Color (adaxial).*—65D.

Reproductive organs:

*Androecium.*—7–9. 8 mm anther/filaments. 1.5–22 mm anther. 53A.

*Gynoecium.*—7 mm, 5 lobed stigma, 2.5–3 mm style.

*Presence or absence of fruits.*—Set fruits.

Spring flowering response period: 7–8 weeks from unrooted cuttings.

Outdoor flower production: Very floriforous non-shattering.

Durability: No weather tolerance claimed.

*Shatter resistance.*—Flowers resistant to shatter.

*Shipping tolerance.*—Stable chlorophyll.

PLANT

Foliage:

*Size (mature foliage).*—8.0–8.5 cm at widest point; 5.0–5.5 cm at narrowest point.

*Leaf stem (pedicles).*—5.0–6.5 cm.

*Form.*—Reniform, cordate.

*Margin.*—Crenate.

*Color (abaxial).*—137A margin. 137B center/base.

*Color (adaxial).*—137C.

*Color (zonation).*—Slight.

*Resistance to botrytis.*—Fair.

General appearance and form:

*Internode length.*—1.0–1.3 cm.

*Branching pattern.*—Basal branching mounded habit.

*Number of branches.*—2–3 branches in a 10 cm pot.

*Height.*—22.86 cm on 18 week old field grown plants.

What is claimed is:

1. A new and distinct Geranium cultivar, substantially as herein described and shown, characterized by its pink-lavender color, mounded habit and non-shattering flower petals.

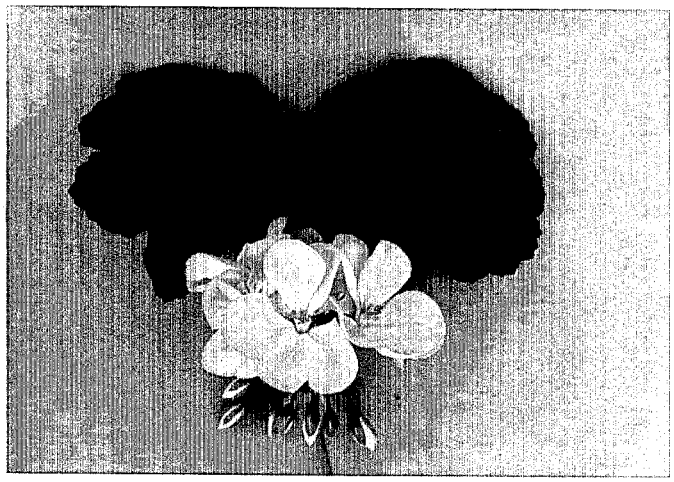
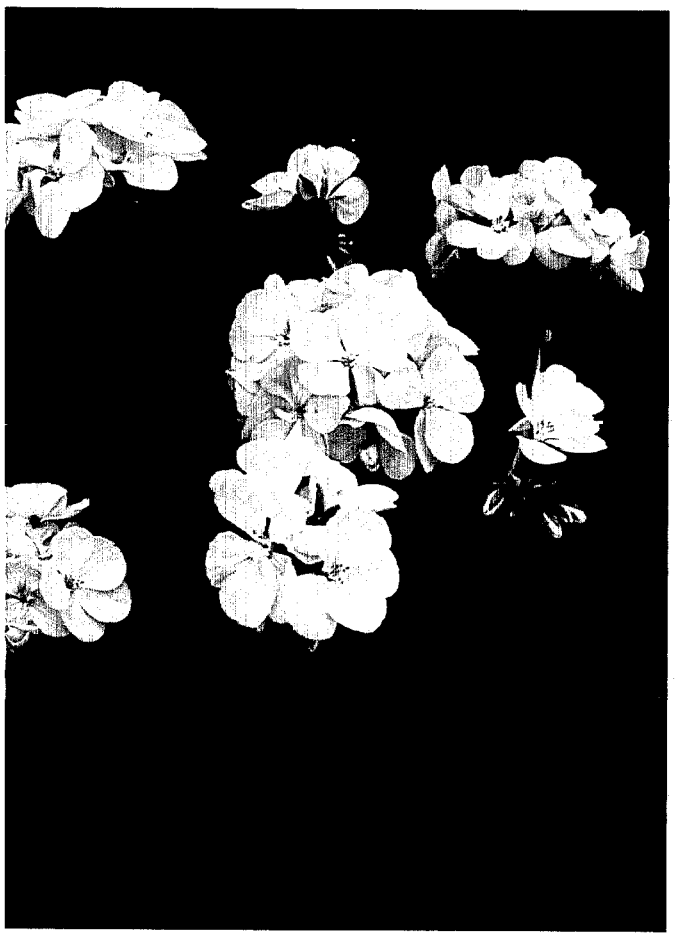

* * * * *